United States Patent [19]

Bellotti et al.

[11] 4,263,808
[45] Apr. 28, 1981

[54] NONINVASIVE PRESSURE MONITOR

[75] Inventors: Marc Bellotti, Winnetka; Richard P. Goldhaber, Libertyville, both of Ill.

[73] Assignee: Baxter Travenol Laboratories, Inc., Deerfield, Ill.

[21] Appl. No.: 23,553

[22] Filed: Mar. 26, 1979

[51] Int. Cl.³ .............................................. G01L 9/04
[52] U.S. Cl. ......................................... 73/714; 73/726; 210/321.1
[58] Field of Search .................. 128/214 E, DIG. 13; 73/725, 727, 726, 715, 730, 714, 731; 422/48

[56] References Cited

U.S. PATENT DOCUMENTS

| 2,927,582 | 3/1960 | Berkman et al. | 128/214 R |
|---|---|---|---|
| 3,017,885 | 1/1962 | Robicsek | 128/214 R |
| 3,157,201 | 11/1964 | Littmann | 137/625.47 |
| 3,240,207 | 3/1966 | Baker et al. | 73/730 |
| 3,418,853 | 12/1968 | Curtis | 73/730 |
| 3,690,312 | 9/1972 | Leibinsohn | 128/214 R |
| 3,713,341 | 1/1973 | Madsen et al. | 73/715 |
| 3,841,157 | 10/1974 | Willock | 128/214 E |
| 3,908,653 | 9/1975 | Kettering | 128/214 R |
| 3,946,724 | 3/1976 | LaBalme | 73/726 |
| 3,946,731 | 3/1976 | Lichtenstein | 128/214 R |
| 4,052,899 | 10/1977 | Longhetto | 73/300 |
| 4,061,035 | 12/1977 | Witzke et al. | 73/726 |

Primary Examiner—Donald O. Woodiel
Attorney, Agent, or Firm—Paul C. Flattery; Garrettson Ellis

[57] ABSTRACT

A noninvasive pressure monitor for measuring the pressure in a hydraulic circuit, such as an extracorporeal blood circuit, includes an aperture sealed by a membrane which offers substantially no resistance to pressure and a pressure sensitive transducer in contact with the membrane for providing a more direct measurement of the pressure.

5 Claims, 5 Drawing Figures

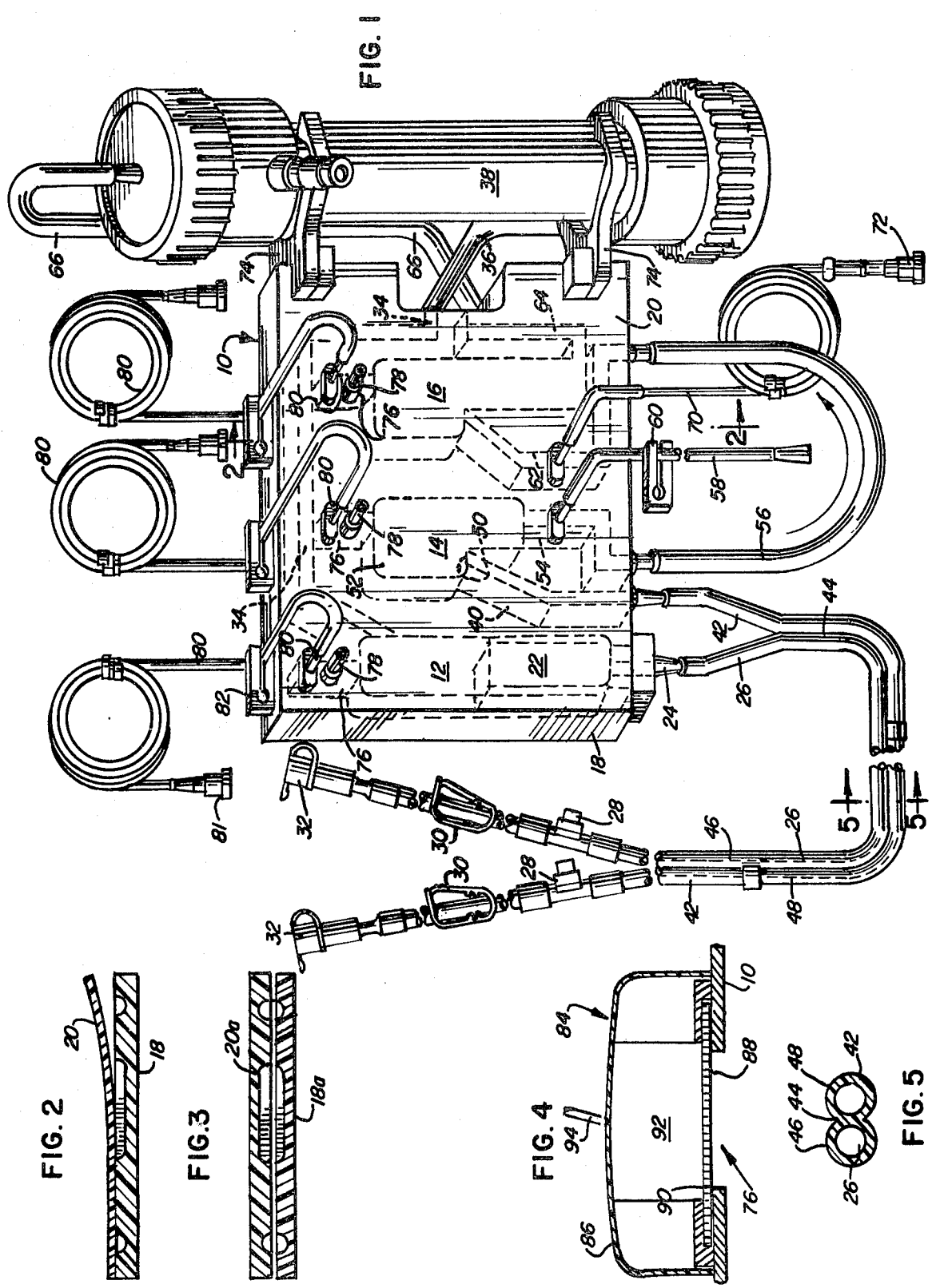

NONINVASIVE PRESSURE MONITOR

BACKGROUND OF THE INVENTION

This invention relates to apparatus used to establish an extracorporeal blood circuit used, for example, to perform hemodialysis. It also relates to monitoring the blood pressure in such a blood circuit and more particularly to noninvasive blood pressure monitors.

Hemodialysis apparatus for artificial kidneys generally comprises a supported, semipermeable membrane made of a cellophane-type material, positioned in a casing to provide a blood flow path along one side of the membrane and a dialysis solution flow path along the other side, for diffusion exchange across the membrane between the blood and the dialysis solution without the direct intermixing of the two liquids.

In the actual hemodialysis process, a considerable number of processing steps are required during the operation of bringing the blood to the hemodialyzer, and withdrawing it from the hemodialyzer for return to the patient. In the presently conventional arterial and venous sets which are used to withdraw blood from a patient, convey it to the dialyzer, and return it again to the patient, bubble traps, filters, sterile access sites for injection needles, and access sites for pressure monitor equipment may all be included on the sets, which primarily comprise flexible, blood compatible plastic tubing. Accordingly, in the present technology of dialysis, two different and separate long, tubular sets are utilized, the arterial set upstream from the dialyzer in terms of blood flow, and the venous set downstream from the dialyzer.

Hence, to set up a dialysis procedure, a dialyzer must be selected, and the nurse must also separately obtain an arterial set and a venous set. The packaging of all of these devices must be opened, and the devices respectively must be connected and assembled together, with other auxiliary equipment being also added to the system. This requires the services of a highly trained technician, who must make a considerable number of connections between the sets and the dialyzer, flawlessly and without error.

In accordance with this invention, a one-piece hydraulic circuit is provided to replace many of the functions of the arterial inlet and outlet sets, and auxiliary equipment. The one-piece hydraulic circuit may be connected to the dialyzer itself at the time of manufacture, if desired. The setup of the dialysis system prior to use is thus greatly simplified, eliminating many of the connections which must be made by the technician at the site of use, which, in turn, reduces the possibility of error, and contamination of the system during the assembly and connection process. Furthermore, the system of this invention is compact and simplified, saving a considerable amount of valuable space around the bed during the dialysis procedure.

Additionally, the blood pressure within the extracorporeal blood circuit is continuously monitored so that adjustments to the system may be made if the pressure falls outside prescribed limits during treatment. It is preferred that the pressure monitoring be accomplished without the pressure sensing device contacting the blood within the extracorporeal blood circuit, thus preventing contamination of the blood as well as preserving the integrity of the pressure sensing device for subsequent use.

The blood pressure is typically monitored at a bubble trapping chamber normally used in an extracorporeal blood circuit. Also used are pressure monitors of the noninvasive type such as disclosed in U.S. Pat. Nos. 3,713,341 and 3,841,157 and 4,077,882. These pressure monitors employ a pressure transfer element which compresses or expands a fixed volume of a compressible fluid such as air in response to pressure changes within a closed chamber. Calibration of such a monitoring device is therefore required to compensate for the compressibility of the fluid and the amount of pressure needed to overcome the inertia of the pressure transfer element itself.

DESCRIPTION OF THE INVENTION

In accordance with this invention, a one-piece hydraulic circuit for use with a blood dialyzer comprises a rigid, unitary member defining spaced first, second and third chambers therein. A first port communicates with the first chamber, and is adapted for connection with a venous line of a patient. A second port also communicates with the first chamber, and is adapted for connection with the outlet of a blood dialyzer.

The second chamber communicates with a third port which in turn is adapted for connection with an arterial line of the patient. The second chamber also communicates with a fourth port adapted for connection with an end of blood pump tubing.

The third chamber communicates with a fifth port which is adapted for connection with the other end of the blood pump tubing. The third chamber also communicates with a sixth port adapted for connection with the inlet of the blood dialyzer.

In the specific embodiment shown, the flow of blood enters the second chamber from the artery of the patient, at which point any bubbles are collected at the top of the chamber, for example, bubbles injected through an injection site into the line to monitor the flow velocity. The fourth outlet port is generally positioned at the bottom end of the chamber to facilitate the bubble trapping characteristic. Blood flows out of the fourth port through pump tubing, which may be installed in a conventional roller pump device to power the flow of blood through the apparatus.

Passing through the pump tubing, the blood enters the fifth port and the third chamber, where an additional bubble trapping function takes place, to prevent bubbles from entering the dialyzer. The sixth port exits from the bottom of the third chamber, and is connected with tubing which, in turn, leads to the blood inlet of the dialyzer.

Passing through the dialyzer, the blood exits from the outlet which, in turn, is in connection with the second port of the first chamber. The blood enters the first chamber, then generally passing through an airblocking filter to prevent infusion of air into the patient. The blood then passes through the first port of the first chamber, which is in communication with tubing connected to the venous system of the patient.

Accordingly, the highly desirable bubble-trapping function, plus a blood filtering function, may be provided by the one-piece hydraulic circuit of this invention.

Additionally, injection-type access sites, for example, for removal of air, are provided, as well as a site for measuring chamber pressure. Also, a saline infusion and a heparin line may be added to the device where desired.

The site for measuring blood pressure within the chamber includes an aperature in the bubble trapping chamber sealed by a liquid impermeable membrane. A pressure sensitive transducer is positioned adjacent the membrane outside the chamber so that its sensing surface is in contact with the membrane. Direct contact between the contents of the chamber and the transducer is thus prevented.

The transducer remains in a fixed position within a housing adjacent the membrane. Pressure exerted against the membrane from within the chamber is also exerted against the sensing surface of the transducer which sends a signal indicative of the pressure to a conventional readout device via electrical wiring. Unlike prior noninvasive pressure monitoring devices, the present system does not rely on deflection of the membrane to transmit the pressure to the transducer thus providing a more direct measurement of the pressure in the chamber.

In the drawings,

FIG. 1 is a perspective view of the one-piece hydraulic circuit member of this invention, connected to a hollow fiber-type dialyzer, and further connected to auxiliary tubing of various types.

FIG. 2 is a transverse sectional view of the one-piece hydraulic circuit member of this invention, taken along line 2—2 of FIG. 1.

FIG. 3 is a similar transverse sectional view of another embodiment of the hydraulic circuit member of this invention.

FIG. 4 is a detailed sectional view of an alternative sensing member as a replacement for member 80.

FIG. 5 is a sectional view taken along line 5—5 of FIG. 1.

Referring to the drawings, hydraulic circuit member 10 is shown to be made of a rigid piece of flat plastic, defining chambers 12, 14 and 16 within the plastic piece.

As shown in FIG. 2, plastic piece 10 may comprise a lower flat plastic plate 18 which defines the chambers and ports utilized herein as cutout portions. Plastic plate 18 may be sealed by a cover member 20 to enclose said cutout portions.

Alternatively, as in FIG. 3, both plastic plate 18a and cover 20a may be equally sized pieces, both defining cutout portions for chambers 12, 14, and 16, and for the various ports.

Chamber 12 may preferably include a blood filter member 22, surrounding a first port or conduit 24, which, in turn, provides communication between chamber 12 and flexible tubing 26, adapted for communication with the vein of a patient. In any conventional manner, venous tubing 26 may contain a sterile injection site 28 for blood sampling or medication, clamp 30, and removable sterile cover 32 for sealing the tubing. Tubing 26 may be connected to a fistula needle for access to the patient, or an arterio-venous shunt, or any other desired means for communication with the patient's venous system.

Chamber 12 also defines a second port or conduit 34 which is shown to define an elongated channel for communication with a blood outlet conduit 36, receiving blood from the blood dialyzer 38. Dialyzer 38 is shown to be commercially available hollow fiber dialyzer in this particular embodiment, although this invention may be used with any type of dialyzer.

Accordingly, blood outflow from the dialyzer 38 enters chamber 12 at an upper end, and passes through filter 22 into venous line 26 for reinfusion to the patient.

Second chamber 14 is in communication through port or conduit 40 with blood tubing 42, which may be in communication with the arterial system of a patient. Tubing 42 also may carry a conventional injection site 28, clamp 30, and sterile cover 32, as well as any other conventional equipment. Also, if desired, tubings 26 and 42 may be integrally connected together by a fine web 44 of plastic material, which may be torn apart as far along the length of the respective tubings 26, 42 as desired, but otherwise which holds the two tubings together in an integral manner, to avoid the confusing and inconvenient separate wandering and coiling of the respective tubes.

Tubes 26 and 42 may be conveniently co-extruded as a single piece to define the frangible web 44 between them. Appropriate indicia such as colored lines 46, 48 may be placed on the respective tubing 26, 42 for identification of the tubing.

Blood from tubing 42 passes through third port 40, preferably at an entry point 50 which is intermediate along the length of chamber 14, to provide an upper area 52 in the chamber for receiving and retaining gas bubbles.

The blood then is withdrawn from chamber 14 downwardly from the lower end through a fourth port or conduit 54 which, in turn, is in communication with a length of blood pump tubing 56. Tubing 56 may be emplaced within a roller-type blood pump for movement of the blood from chamber 14 to chamber 16, and to power the blood flow through the entire system.

If desired, saline solution infusion line 58, controlled by clamp 60, may communicate in sterile manner with port 54 for use as desired.

The blood from tubing 56 enters fifth port or conduit 62, which leads to chamber 16, communicating with the chamber at a mid-point thereof in a manner similar to entry point 50, and for the similar purpose of providing a bubble-trapping capability to the chamber.

Blood is withdrawn from chamber 16, impelled by the action of a blood pump on tubing 56, through the sixth port or conduit 64, which, in turn, communicates with an inlet line 66 leading into the blood inlet of the dialyzer 38.

A heparin administration line 70 may be provided in communication with port 62 if desired, carrying a sterile end seal 72 for connection with any desired heparin administration device for administering measured quantities of heparin over a period of time to the blood circuit.

Accordingly, blood enters from the patient's arterial system through tubing 42, passing through port 40 to chamber 14 for bubble removal, and from there to pump tubing 56 through port 54.

Impelled by the blood pump, the blood is forced onwardly through port 62 into chamber 16 for additional bubble removal, and from there through port 64 into the dialyzer 38. Dialyzed blood passes along port 34 into chamber 12. Then, the blood passes through filter 22, through port 24, and into venous tubing 26 for return to the patient.

Gripper members 74 are carried by hydraulic circuit member 10 for grasping, as shown, the dialyzer 38, to provide a convenient, one-piece structure including both the dialyzer and much of its circuitry. The entire structure may have a hanger or attachment member (not shown) for hanging or clamping on an IV pole or the like as desired.

Each of the chambers 12, 14, 16 defines an upper projecting channel 76. Connected to this channel in each case is a sealed injection site member 78, which may include a latex member compression fitted into a tubular member in a manner similar to the injection site members which are in present commercial use on the arterial and venous sets for dialysis sold by the Artificial Organs Division of Travenol Laboratories, Inc., Deerfield, Illinois. Excess air trapped in the chambers may be removed by a needle and syringe through site 78.

Tubing 80 is also in communication with upper projecting channel 76 in each case. Sealed end 81 may be opened and connected to a manometer or other pressure measuring device to obtain a direct measurement of the pressure within chambers 12, 14 or 16. Clamp 82 is also provided to seal tubing 80 when not in use. As an alternative structure to replace tube 80 with its direct connection to each of the chambers 12, 14 or 16, a pressure-sensing member 84 may be provided which measures the pressure of the respective chambers in a noninvasive manner.

As shown in FIG. 4, pressure-sensing member 84 comprises a housing 86 which fits over an aperture 88 in part of the wall of hydraulic circuit member 10 which is in communication with channel 76. A liquid-impermeable, flexible membrane 90 is positioned across aperature 88, and adjacent the sensing surface of a transducer 92, which is adapted to sense the pressure exerted against its sensing surface, in response to positive or negative pressure in the channel 76.

The housing 86 prevents movement of the transducer 92 thereby maintaining contact between the membrane 90 and the sensing surface of the transducer 92 while the pressure is being monitored. As pressure is exerted against the membrane 90, which in turn is exerted against the sensing surface of the transducer 92, the transducer 92 sends a signal to a conventional readout device via electrical line 94 so that the pressure can be monitored.

The membrane 90 is made of a thin, elastic material which is relatively incompressible such as latex. It also offers substantially no resistance to the pressure exerted against it. The membrane 90 isolates the transducer 92 from the contents of the circuit member 10. The same pressure exerted against the membrane 90 is therefore transmitted to the sensing surface of the transducer 92. The transducer 92 directly measures the pressure within the chamber 10 rather than movement of the membrane 90. Calibration of the transducer 92 to account for the amount of pressure required to move the membrane 90 is not necessary, thereby simplifying the procedure to set up the pressure monitor 84 of the present invention.

The setup procedure with the present invention is relatively easy. When there is no blood in the hydraulic circuit, only atmospheric pressure is exerted against the membrane 90. The readout device may be adjusted to a neutral position to account for this atmospheric pressure. Then, as blood enters the circuit member 10, the pressure exerted against the membrane 90 changes. Since the membrane 90 offers substantially no resistance, the same pressure is exerted against the sensing surface of the transducer 92 which communicates this change to the readout device along the electrical line 94. The transducer 92 continuously measures the pressure being exerted against its sensing surface. Thus as the pressure changes within the circuit member 10, different output signals are sent from the transducer 92.

Very accurate transducers employing electronic strain gauges, such as Model No. AB-25 manufactured by Data Instruments, Inc. of Lexington, Mass., may be used with the present invention. The use of such a sensitive device in accordance with the present invention allows the pressure to be monitored with a high degree of accuracy without depending upon movement of a diaphragm.

After treatment is completed, the housing 86 can be removed. The transducer 92 can therefore be placed adjacent the membrane of another hydraulic circuit member to monitor the pressure during subsequent treatments.

While the pressure monitoring member 84 of the present invention has been described as measuring the pressure within chambers 12, 14, 16 the apparatus 84 could be adapted for use at any appropriate location in a hydraulic circuit.

The above has been offered for illustrative purposes only, and is not for the purpose of limiting the invention of this application, which is as defined in the claims below.

What is claimed is:

1. A noninvasive pressure monitoring device for measuring the pressure in an extracorporeal blood circuit comprising:
   a bubble trap having an aperture;
   a liquid impermeable membrane sealing said aperature,
   said membrane being capable of transmitting pressure while offering substantially no resistance to such pressure;
   a pressure sensitive transducer in contact with the surface of said membrane outside of said bubble trap; and
   a housing for maintaining contact between said transducer and said membrane.

2. The noninvasive pressure monitoring device of claim 1 wherein said housing is connected to said chamber for holding said transducer in a stationary position in contact with the surface of said membrane.

3. The noninvasive pressure monitoring device of claim 1 wherein said membrane comprises a thin, elastic sheet of latex and said transducer is an electronic strain gauge having an output signal indicative of the pressure.

4. The noninvasive pressure monitoring device of claim 1 further comprising a readout device in communication with the output signal of said transducer.

5. The noninvasive pressure monitoring device of claim 1 wherein said membrane comprises a thin, elastic sheet of latex:
   said transducer is an electronic strain gauge having an output signal indicative of the pressure in said bubble trap;
   and further comprising a readout device in communication with the output signal of said transducer.

* * * * *